United States Patent [19]

Peterson

[11] 4,449,968

[45] * May 22, 1984

[54] POULTRY VACCINATION SYSTEM

[75] Inventor: Walter L. Peterson, Gainsville, Ga.

[73] Assignee: Select Laboratories, Inc., Gainesville, Ga.

[ * ] Notice: The portion of the term of this patent subsequent to Feb. 23, 1999 has been disclaimed.

[21] Appl. No.: 350,597

[22] Filed: Feb. 22, 1982

Related U.S. Application Data

[63] Continuation-in-part of Ser. No. 241,495, Mar. 9, 1981, Pat. No. 4,316,464.

[51] Int. Cl.³ .......... A61M 11/00

[52] U.S. Cl. .......... 604/24; 604/290

[58] Field of Search .......... 128/200.14, 200.18, 128/200.21-200.23; 604/48-49, 54, 93, 259, 604/261, 289-290, 294, 310, 24; 119/156, 158-160, 1 _

[56] References Cited

U.S. PATENT DOCUMENTS

| | | | |
|---|---|---|---|
| 974,252 | 11/1910 | Fish | 119/159 |
| 2,847,993 | 8/1958 | Woodruff | 128/191 |
| 2,910,407 | 10/1959 | Mitchner | 167/78 |
| 2,984,240 | 5/1961 | Eames | 128/185 |
| 3,076,745 | 2/1963 | Eames | 167/53.1 |
| 3,148,649 | 9/1964 | Moore et al. | 119/1 |
| 3,502,079 | 3/1970 | Simmons et al. | 128/253 |
| 3,704,688 | 12/1972 | Wilson | 119/22 |
| 3,777,752 | 12/1973 | Godwin | 128/173 |

OTHER PUBLICATIONS

"Vaccination Against Pneumoencephalitis (Newcastle Disease) by Atomization or Nebulization in Incubators and Chick Boxes with the B, Virus", by E. P. Johnson & W. P. Gross, Sep. 1952, Veterinary Medicine p. 364-366, 371.

Micron West Inc., P.O. Box 19698, Houston, Tex. 77024, (713) 932-1405, Telex 79 251 MICRONW HOU.

Spray Vaccination: Immunizing Poultry against Newcastle Disease, Salsbury Laboratories, Charles City, Iowa 50616, Printed U.S.A. A-SPB-300-85.

Spray the New, Efficient Way with the "ULVAFAN" the Ultimate Vaccination Sprayer, Salsbury Laboratories, Charles City, Iowa 50616, Printed U.S.A. 1-91-01-8007.

*Primary Examiner*—Kyle L. Howell

*Assistant Examiner*—Angela D. Sykes

*Attorney, Agent, or Firm*—Thomas & Kennedy

[57] ABSTRACT

Baby chicks are loaded in an open top container 32 and the container is moved into an open ended cabinet 18. In response to the movement of the container into the cabinet, a dose of vaccine is emitted through at least one nozzle 42 supported in the upper portion of the cabinet. The spray emitted from the nozzle is of a droplet size large enough to fall onto the chicks in the container substantially without remaining airborne long enough to be inhaled by the chicks.

13 Claims, 4 Drawing Figures

FIG. 2
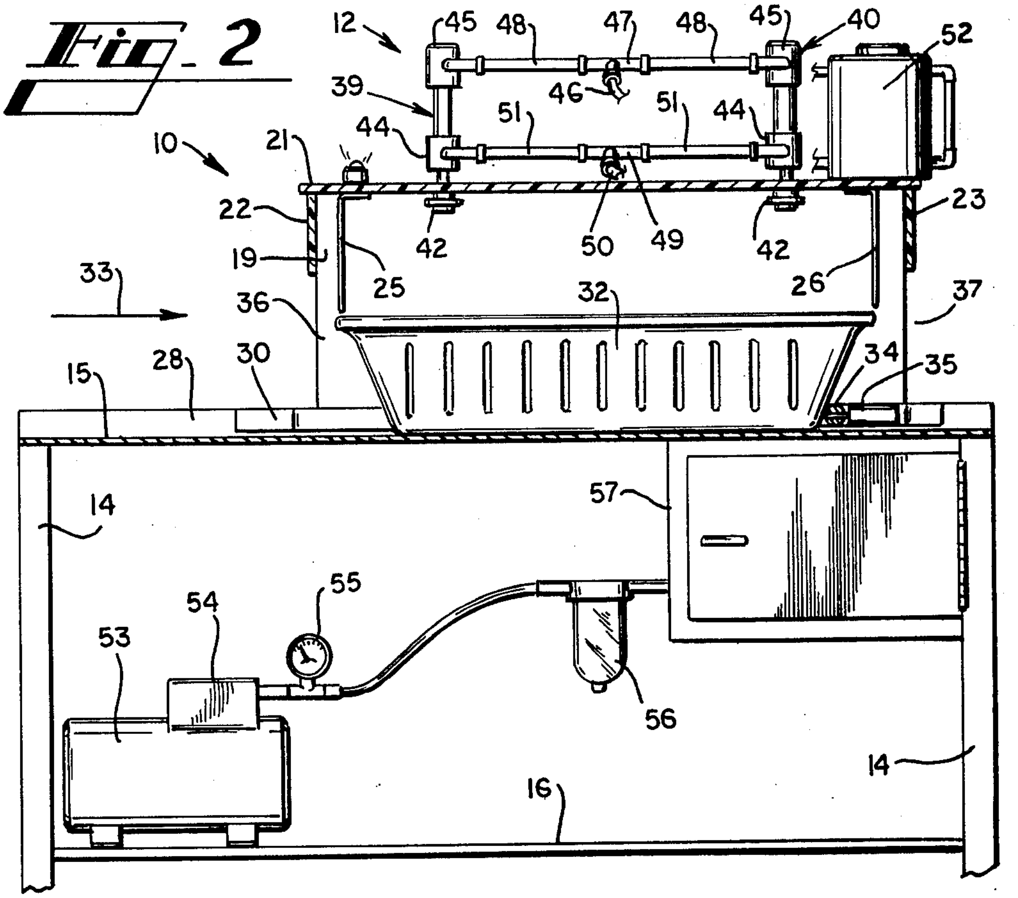
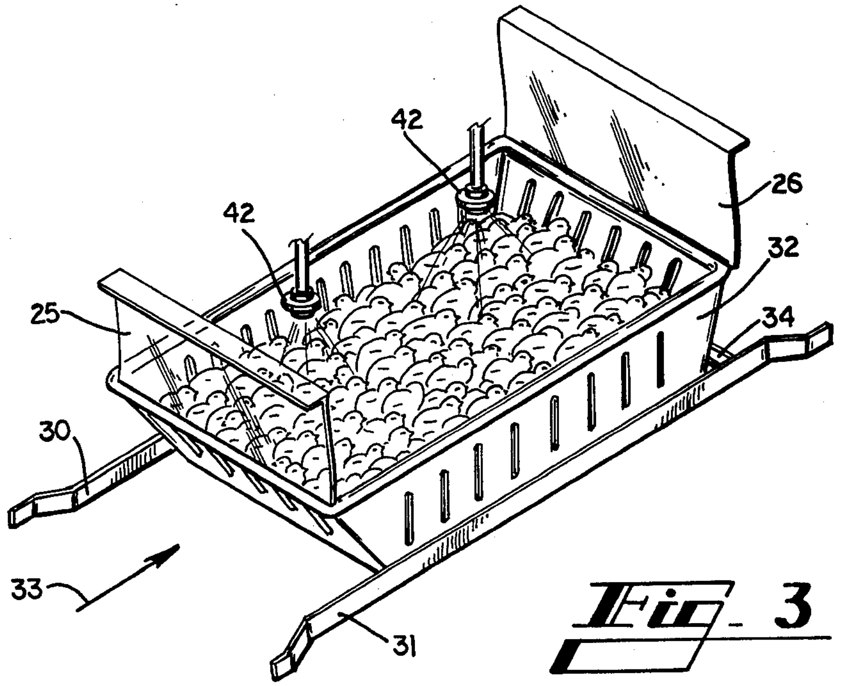
FIG. 3

POULTRY VACCINATION SYSTEM

CROSS REFERENCE

This is a continuation-in-part of U.S. Patent Application Ser. No. 241,495 filed Mar. 9, 1981, now U.S. Pat. No. 4,316,464, issued Feb. 23, 1982.

BACKGROUND OF THE INVENTION

It is customary to vaccinate poultry that is raised for commercial purposes against various respiratory diseases such as Newcastle's Disease and infectious brochitis. Usually the birds are vaccinated when they are ten to twelve days old, after they have been moved from the hatchery to the brooder house.

Some of the methods used to vaccinate baby chicks have been to physically inject vaccine into the body of the chick with a syringe, to spray live virus vaccine into the mouth of a chick as the upper beak is foreshortened in a "de-beaking" process, and to place a drop of vaccine with an "eye dropper" into an eye of the chick so that the vaccine enters the eye opening of the chick and passes through the nasal passage of the chick and into the respiratory system. These procedures require the chicks to be handled individually and require a long time for a person to administer vaccine. Also, the spraying of vaccine into the mouth of a chick sometimes results in secondary bacterial infections in the lungs of the chick and causes lung disease and death. Another method of vaccination is to mix vaccine with the drinking water for chicks. This has proven to be about fifty percent effective in properly administering the vaccine to the chicks. Another method of vaccinating chicks that was used for a short duration was to place a multiple number of the chicks in a container and form a fine mist of liquid live virus vaccine in the container about the chicks so that the chicks inhaled the vaccine. This method of vaccinating chicks resulted in excessive vaccine reaction of the chicks and caused lung disease and death of a substantial percent of the chicks.

SUMMARY OF THE INVENTION

Briefly described, the present invention comprises a poultry vaccination system wherein newly hatched baby chicks are loaded into conventional open top containers at a hatchery and the containers are moved through an open ended cabinet. A dose of vaccine is moved from a supply and sprayed downwardly from within the cabinet into the open top containers and onto the chicks. Most of the spray droplets are of a size large enough to fall onto the chicks substantially without remaining airborne long enough to be inhaled by the chicks. The spray is directed in a downwardly inclined pattern so that the droplets are likely to make contact with the upper body portions of the chicks in the open top container, particularly with the eyes of the chicks. Some of the droplets come to rest on other parts of the upper body portions of the chicks, and the natural movements of the chicks in the open top container tend to spread the droplets from the upper body portions of the chicks to the eyes of the chicks, as by the head and eyes of a chick making contact with a droplet of vaccine on the upper body portion of an adjacent chick. The vaccine tends to be introduced into the sinus and respiratory systems of the chicks by passing from the eyes of the chicks into the nasal passages. Moreover, the chicks are inclined to peck at the droplets of vaccine resting on adjacent ones of the chicks, so that the vaccine is spread through the mouth to the respiratory system of some of the chicks. Furthermore, some of the chicks respond to the presence of the droplets on their upper bodies by shaking their heads and upper bodies, thereby causing the droplets to splash about adjacent ones of the other chicks, tending to help disseminate the vaccine into the eyes of adjacent ones of the other chicks.

While a small amount of the vaccine of the spray might emerge from the spray nozzles in a fine mist, the small amount ejected from the nozzles as a mist has not been found to be sufficient to interfere with the normal respiratory function of the chicks. Moreover, the open top containers and the chicks carried thereby are removed from the spray cabinet as soon as practical after the vaccine has been sprayed on the chicks so that any airborne mist is ventilated away from the chicks during the movement of the container.

Thus, it is an object of the present invention to provide a poultry vaccination system which rapidly and reliably administers live virus vaccine to baby chicks, without having to individually handle each baby chick.

Another object of this invention is to provide a poultry vaccination system wherein vaccine is administered to a multiple number of baby chicks substantially without hazard of harming the chicks from overdosing the chicks or from manually handling the chicks.

Another object of the invention is to provide a means of simultaneously spraying vaccine into the eyes of a multiple number day old baby chicks.

Another object of the invention is to provide a system for simultaneously administering vaccine to the eyes of a multiple number of baby chicks.

Other objects, features and advantages of the present invention will become apparent upon reading the following specification, when taken in conjunction with the accompanying drawings.

BRIEF DESCRIPTION OF THE DRAWINGS

FIG. 2 is a side elevational view of the poultry vaccination cabinet, showing an open top chick container positioned in the cabinet.

FIG. 3 is a perspective illustration of an open top chick container filled with baby chicks and showing how the chick container is positioned beneath the spray nozzles and between the end curtains and side guide rails of the poultry vaccination cabinet.

DETAILED DESCRIPTION

Figure 1:
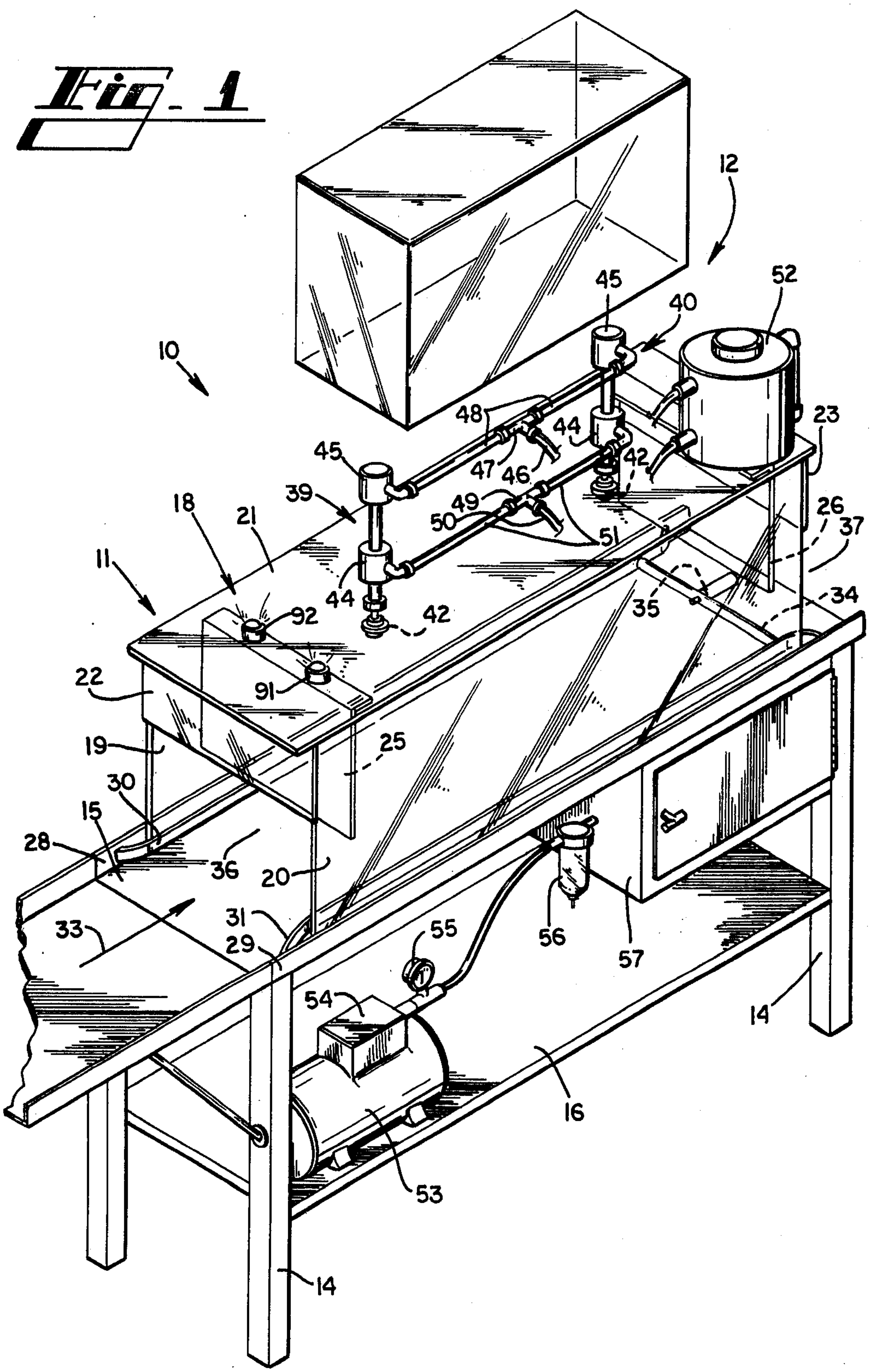
FIG. 1 is a perspective illustration of the poultry vaccination cabinet and related equipment of the poultry vaccination system, showing the protective top suspended above the cabinet.

Referring now in more detail to the drawings, in which like numerals indicate like parts throughout the several views, FIG. 1 illustrates the poultry vaccination system 10 which includes a cabinet assembly 11 having a vaccine control system 12 mounted thereon. The cabinet assembly 11 comprises upright support legs 14 that support at their upper ends a horizontal platform 15. A lower support platform 16 also extends between the support legs 14, and a transparent, open ended cabinet 18 is mounted on horizontal platform 15.

Cabinet 18 comprises parallel upright sidewalls 19 and 20 and a horizontal top wall 21 which merges at its side edge portions with the upper edge portions of the sidewalls. The horizontal platform 15 comprises the lower wall and conveyor platform of the cabinet 18. Upper end wall sections 22 and 23 extend a short way down from the top wall 21 at the ends of cabinet 18, so that the spaces between the lower edges of the upper end wall sections 22 and 23 and the horizontal platform 15 remain open and comprise inlet opening 36 and exit opening 37. Flexible curtains 25 and 26 are suspended from top wall 21 and are spaced inwardly of the cabinet from upper end wall sections 22 and 23. The flexible curtains 25 and 26 extend downwardly within the cabinet to a lower level than the lower edges of upper end wall sections 22 and 23. In the disclosed embodiment the cabinet 18 and flexible curtains 25, 26 are fabricated from transparent materials so that the chicks and chick containers moved to a position inside the cabinet can be visually observed from outside the cabinet.

Side flanges 18 and 29 extend upwardly from the edges of horizontal platform 15, and the lower edges of side walls 19 and 20 of cabinet 18 are positioned inside the side flanges 28 and 29. Guide rails 30 and 31 are attached at their ends to side flanges 28 and 29, and the end portions of the guide rails are curved so that the center portion of each guide rail extends inside the side walls 19 and 20 of the cabinet 18. Thus, the side flanges 28 and 29 and guide rails 30 and 31 define a path of movement as indicated by arrow 33 for open top chick containers 32 (FIGS. 2 and 3). The lower portions of the chick containers 32 are of a width slightly less than the space between guide rails 30 and 31, the upper portions of the chick containers are of a length approximately the same as the distance between flexible curtains 25 and 26, and the chick containers are of a height slightly less than the distance between horizontal platform 15 and the lower edges of flexible curtains 25 and 26. A stop bar 34 is positioned at the exit opening 37 of cabinet 18, so that when a chick container 32 is moved through the inlet opening into the cabinet 18 the lower portion of the chick container will engage and its movement will be stopped by stop bar 34 and the chick container will be centrally located within the cabinet 18 (FIG. 2). Control valve 35 is mounted behind stop bar 34 and its valve plunger extends through an opening in the stop bar. The plunger of control valve 35 is engaged by the leading end of a container and opens the value, thereby detecting the movement of a chick container 32 into abutment with stop bar 34.

The open top chick containers 32 are of standard design and usually are to be filled with 100 baby chicks, as illustrated in FIG. 3. This contains the chicks in a crowded condition in which the chicks are in physical contact with one another.

As best illustrated in FIG. 2., the portion of the vaccine control system 12 that is mounted on cabinet 18 comprises a pair of spray nozzle assemblies 39 and 40 mounted on the top wall 21 of the cabinet. The spray nozzle assemblies 39 and 40 each include a nozzle element 42 supported in the upper portion of cabinet 18, a valve 44 positioned above the nozzle 42, and a valve lifter 45 mounted on the valve 44. Air supply conduit 46 communicates through Tee connector 47 and branch conduit 48 with the valve lifters 45, and vaccine supply conduit 50 communicates through Tee connector 49 with branch conduits 51 with valves 44.

The nozzle elements 42 in the disclosed embodiment of the invention have a nozzle throat of approximately 0.039 inches diameter for a conical spray pattern at an angle of approximately 80°. With a back pressure of between 40 and 45 psi, the vaccine, which has a viscosity about the same as water, moves through the nozzle at a rate of about one gallon per hour. The supply of vaccine is maintained in container 52 which is pressurized during operation of the system. Transparent top 59 is positioned about the portion of the vaccine control system that is mounted on the top of the cabinet.

The remaining portion of the vaccine control system is located below horizontal platform 15 and includes an oil-less compressor 53, air pressure regulator 54, air pressure gauge 55, air filter 56, and most of the elements of FIG. 4 which are located in control cabinet 57. Air pressure regulator 54 is to be adjusted so as to cause air at a pressure between 40 and 45 psi to be transmitted to the control system. If desired, an air pressure tank 58 (FIG. 4) can be used in combination with the compressor so as to avoid having the compressor cycle on and off so frequently during the operation of the system.

Figure 4:
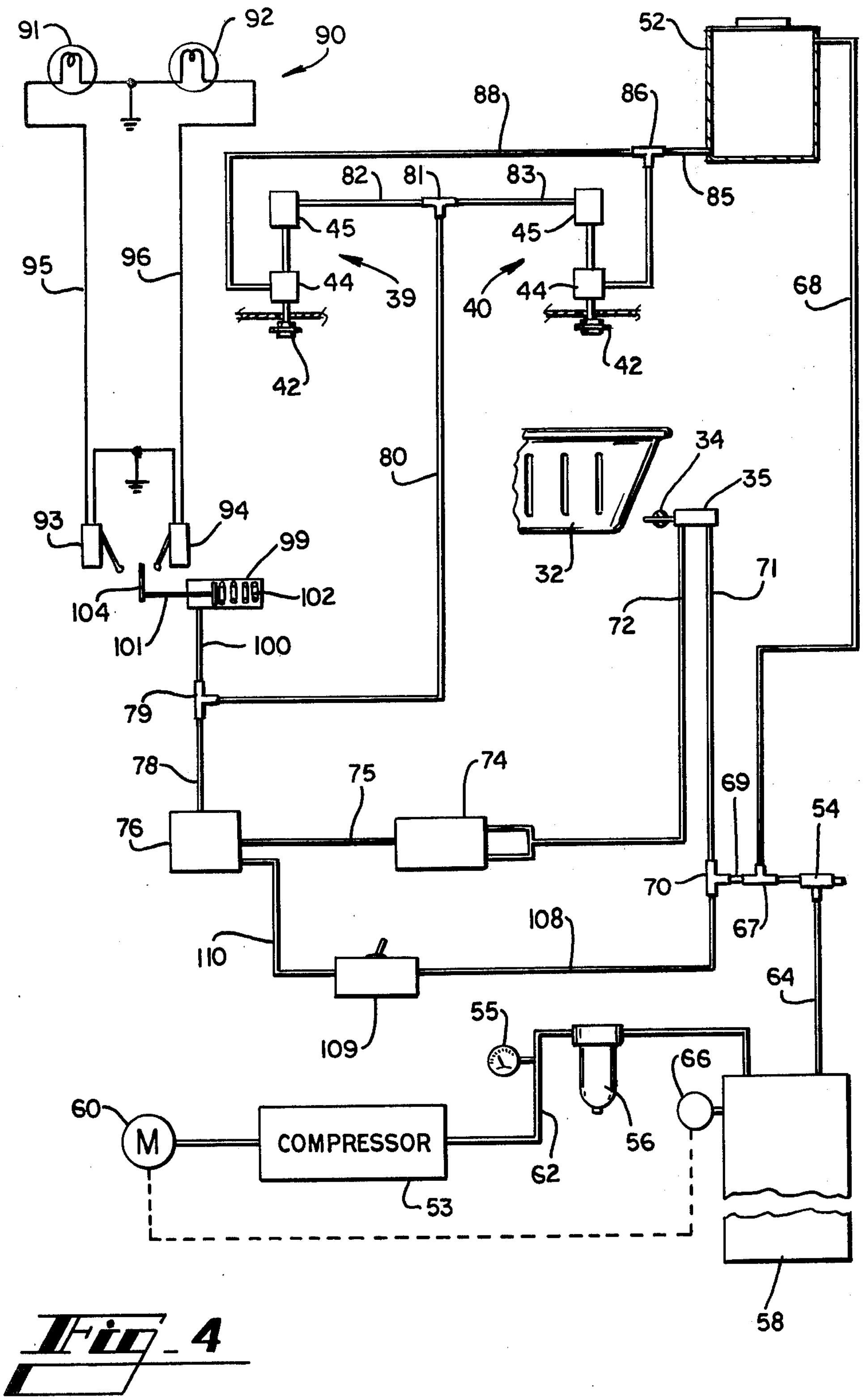
FIG. 4. is a schematic illustration of the fluid and electrical control system of the poultry vaccination system.

As illustrated in FIG. 4, the vaccine control system comprises an electric motor 60 that drives air compressor 53. The outlet conduit 62 of air compressor 53 extends through air filter 56 and then to an optional air pressure tank 58, and then through conduit 64 to air regulator 54. Compressor 53 supplies air under pressure to air pressure tank 58 at approximately 80 psi. Air regulator 54 reduces the air pressure to a level between 40 and 45 psi. Control valve 66 detects the pressure of air in air pressure tank 58 and energizes and deenergizes motor 60 in response to low and high air pressures present in the tank.

Air passes from air regulator 54 through T-connection 67 to Air delivery conduit 68 which supplies air under pressure at between 40 and 45 psi to the top of vaccine supply container 52. The other air delivery conduit 69 connected to T-connection 67 directs air through Tee connection 70, and one of the supply conduits 71 extends from T-connection 70 to control valve 35. When control valve 35 is actuated by the abutment of an open top chick container 32 thereagainst, air under pressure is communicated from control valve 35 through air supply conduit 72 to delay valve 74. Delay valve 74 is a normally on and delayed close valve, so that when air is transmitted through air supply conduit 72 to delay valve 74, air is immediately passed through delay valve 74 to air supply conduit 75. After a predetermined lapse of time, delay valve 74 cuts off the flow of air to air supply conduit 75.

When a flow of air is communicated from delay valve 74 through air supply conduit 75 to double check valve 76, air is immediately transmitted through air supply conduit 78, Tee connection 79, air supply conduit 80, Tee connection 81 and air supply conduits 82 and 83 to valve lifters 45 of nozzles 42. When the valve lifters 45 of the nozzles 42 are charged with air the air does not pass through the nozzles and into the cabinet but the air simply opens the liquid passageways of the nozzles so as to permit the liquid vaccine to be transmitted therethrough and sprayed down into the cabinet [FIGS. 1 and 2].

Vaccine supply conduit 85 communicates at one end with the lower portion of vaccine supply container 52, and also communicates through Tee connector 86 with vaccine supply conduits 87, 88. Vaccine conduits 87 and 88 communicate with valves 44 of spray nozzles 42. Thus, the valves 44 of spray nozzles 42 are continuously charged with vaccine under pressure. When air under pressure is communicated to the valve lifters 45 of nozzles 42 and the nozzles open, a stream of vaccine will flow through each nozzle, and the nozzles 42 convert the stream of vaccine into a coarse spray that is directed in a downwardly inclined direction toward the chicks in the chick container 32 positioned beneath the nozzles 42.

The duration of the spray cycle is determined by delay valve 74. When delay valve 74 reaches the end of its cycle and cuts off the communication of air through air delivery conduit 75, the air pressure communicated through valve 76, and air delivery conduits 78, 80, 82 and 83 terminates and air actuated valves 44 close. This terminates the flow of vaccine through the nozzles 42. The delay period of delay valve 74 is adjusted so that the air actuated nozzles 42 remain open for a predetermined time. This time interval, together with the aperature opening of the nozzles, and together with the back-pressure of vaccine charged to the nozzles is calculated to deliver a predetermined quantity or dose of vaccine through each nozzle.

Light indicator system 90 comprises a pair of incandescent bulbs 91 and 92 that are controlled by on/off switches 93 and 94 and the electrical conductors 95 and 96. Switch actuator 98 comprises single acting cylinder 99 that is spring urged in one direction toward switch 93 and which is pressure urged in the other direction towards switch 94. Air delivery conduit 100 communicates with Tee connector 79 so that when delay valve 74 transmits air through air delivery conduit 75, valve 76, air delivery conduit 78, Tee connector 79 and air delivery conduit 100, plunger 101 of switch actuator 98 retracts within its cylinder against the bias of coil compression spring 102. The protrusion 104 of plunger 101 moves away from switch 93, thereby opening switch 93 and moves towards switch 94, thereby closing switch 94. This opens the circuit to incandescent lamp 91 and closes the circuit to incandescent lamp 92. This gives the operator an indication that vaccine is being sprayed by the system to the chicks.

When the delay valve 74 times out, air pressure is no longer communicated to cylinder 99, and coil commpression spring 102 distends plunger 101, opening switch 94 and closing switch 93. Thus, the circuit to incandescent lamp 92 is opened and the circuit to incandescent lamp 91 is closed, providing an indication to the operator that the spray cycle has been completed and the apparatus is ready to receive another tray full of baby chicks.

In the event that it is desirable to cause vaccine or other liquid to be dispensed through air actuated spray nozzles 42 without having to move a container of chicks into the cabinet, the delay valve 74 can be bypassed and the system can be operated manually. Air delivery conduit 108 communicates with Tee connection 70 and with manual valve 109. Manual valve 109 communicates through air delivery conduit 110 to double check valve 76, so that the conduits downstream from valve 76 can be charged with air pressure, as previously described.

While horizontal platform 15 has been indicated as being a flat work surface, it will be understood by those skilled in the art that platform 15 can comprise a conveyor belt, a roller conveyor or other means for guiding and/or moving chick containers in a horizontal direction through transparent open ended cabinet 18. Additionally, stop bar 34 is illustrated as being a rigid member extending between guide rails 30 and 31; however, it should be understood that the stop bar can comprise a movable member that enters the path of the chick containers so as to stop the movement of the chick containers through the cabinet, and then retracts from the path of the chick containers so as to permit the chick containers to move out the exit opening of the cabinet.

When the spray cycle has been completed, it is desirable to remove the chick containers from the cabinet so that the next chick container can be inserted into the cabinet. The sprayed chick containers usually are stacked one atop the other and the side vent openings in the chick containers permit proper ventilation for the chicks.

After the spray cycle has been completed, the droplets of vaccine will have been sprayed to the upper body portions of the chicks in each chick container. Some of the droplets will make direct contact with the eyes of the chicks, thus causing some of the chicks to be directly vaccinated. Other droplets will come to rest on the upper body portions of the chicks. The natural movements of the chicks in the chick container and the crowded conditions of the chicks in the container result in some of the droplets being rubbed from the upper body portions of the chicks into the eyes of adjacent chicks. Additionally, some of the chicks respond to the spray by shaking their heads and upper body portions. This causes some of the droplets to be splashed into the eye openings of adjacent chicks. When the vaccine enteres the eye opening of a chick, it tends to migrate through the nasal passages of the chick to be ingested by the chick. Also, some of the chicks tend to peck at droplets of vaccine that are supported on the upper body portions of adjacent chicks. This results in some of the vaccine being ingested orally by the chicks. It is desirable to retain the chicks in the chick containers for a period sufficient for the natural body motions and instincts of the chicks to disseminate the vaccine among the chicks in this manner.

The size of the liquid orifice of the air actuated vaccine spray nozzles 42, together with the pressure of the vaccine charged to the nozzles are chosen so as to result in a large percentage of the vaccine being dispersed in droplets with diameters between 90 microns and 190 microns. It is estimated that up to 80 percent of the droplets of vaccine is dispersed in this diameter range. Of course, slight variation in nozzle configuration and variation in the back pressure of the vaccine is likely to change the droplet size of the vaccine as it is discharged into the cabinet. It has been found that less than one-tenth of one percent of the droplets are discharged by the nozzles in the inhalation region of 8 microns or less in diameter.

While this invention has been described in detail with particular reference to a preferred embodiment thereof, it will be understood that variations and modifications can be effected within the scope and spirit of the envention as described hereinbefore and as defined in the appended claims.

I claim:

1. A method of vaccinating poultry comprising placing a multiple number of chicks in an open top container, moving the container along a path until the container is located beneath at least one spray nozzle, ejecting a vaccine spray from the nozzle downwardly onto the upper portions of and into the eyes of the chicks in droplets wherein at least about 80 percent of the droplets are in a size range from about 90 microns in diameter to about 190 microns in diameter, removing the container from beneath the spray nozzle, and retaining the chicks in the container for a period sufficient for the normal movement of the chicks with respect to one another to cause some of the droplets of vaccine on the bodies of some of the chicks to make contact with the bodies of adjacent chicks.

2. The method of claim 1 and wherein the step of moving the container along a path until the container is located beneath at least one spray nozzle comprises moving the container through one open end of and into an open ended cabinet to a position between movable curtains at the open ends of the cabinet and against an abutment.

3. The method of claim 1 and wherein the step of ejecting a vaccine spray is initiated in response to moving the container to a predetermined position beneath the spray nozzle.

4. The method of claim 1 and wherein the step of moving the container along a path until the container is located beneath at least one spray nozzle comprises moving the container through one open end of and into a transparent cabinet having thus open ends against an abutment, and wherein the step of removing the container from beneath the spray nozzle comprises moving the container through the other open end of and out of the open ended transparent cabinet.

5. A method of vaccinating poultry comprising the steps of placing a multiple number of chicks in containers, moving the containers in series adjacent a spray nozzle, ejecting a vaccine spray from the nozzle toward the chicks in each container in droplets in which less than one percent of the droplets are airborne long enough to be inhaled by the chicks, and removing the containers from adjacent the nozzle.

6. The method of claim 5 and wherein the step of ejecting the vaccine spray from the nozzle comprises ejecting the vaccine spray with at least about 80% of the droplets between about 90 microns and 190 microns in diameter.

7. The method of claim 5 and wherein the step of ejecting the vaccine spray comprises urging a liquid stream without air entrained therein through the nozzle.

8. A method of vaccinating poultry comprising the steps of placing a multiple number of chicks in containers, moving the containers in series adjacent a spray nozzle, ejecting a vaccine spray from the nozzle toward the chicks in each container in droplet sizes large enough to fall onto the chicks in each container substantially without remaining airborne long enough to be inhaled by the chicks.

9. Apparatus for vaccinating poultry comprising a cabinet defining at least one open end for receiving chick containers said cabinet having an upper portion and a lower portion, at least one spray nozzle supported in the upper portion of said cabinet for spraying vaccine downwardly into chick containers moved into the cabinet in droplets of a size large enough to fall on chicks in the chick containers substantially without remaining airborne long enough to be inhaled by the chicks, and spray control means for moving vaccine through said spray nozzle.

10. The apparatus of claim 9 and wherein said spray control means comprises means for initiating the spray of vaccine upon engagement of valve means by a chick container as the chick container moves beneath said spray nozzle.

11. Apparatus for vaccinating poultry by contacting the eyes of chicks with a vaccine comprising means for supporting an open top chick container beneath at least one spray nozzle, control means for moving vaccine through said spray nozzle and to form the vaccine in a droplet size large enough to fall onto the chicks in the chick container substantially without remaining airborne long enough to be inhaled by the chicks.

12. The apparatus of claim 11 and wherein said control means is responsive to the movement of a chick container to a position beneath the spray nozzle to move the vaccine through the spray nozzle.

13. Apparatus for vaccinating poultry comprising a cabinet defining at least one open end for receiving chick containers, said cabinet having an upper portion and a lower portion, at least one spray nozzle supported in the upper portion of said cabinet for spraying vaccine downwardly into chick containers moved into the cabinet in droplets of a size large enough to fall on chicks in the chick containers substantially without remaining airborne long enough to be inhaled by the chicks, said spray nozzle being sized and shaped to emit at least 80% of the droplets of vaccine between about 90 microns and 190 microns in diameter, and spray control means for moving vaccine through said spray nozzle.

* * * * *